(12) United States Patent
Marczyk et al.

(10) Patent No.: US 9,144,435 B2
(45) Date of Patent: Sep. 29, 2015

(54) CLAMP FOR MALE CIRCUMCISION AND RELATED METHOD OF USE

(75) Inventors: Stanislaw Marczyk, Stratford, CT (US); Emily Grace-Anne Gumkowski, Durham, CT (US); Ross D. Segan, Guilford, CT (US)

(73) Assignee: Covidien LP, Mansfield, MA (US)

( * ) Notice: Subject to any disclaimer, the term of this patent is extended or adjusted under 35 U.S.C. 154(b) by 168 days.

(21) Appl. No.: 13/468,244

(22) Filed: May 10, 2012

(65) Prior Publication Data

US 2012/0303041 A1    Nov. 29, 2012

Related U.S. Application Data

(60) Provisional application No. 61/490,679, filed on May 27, 2011.

(51) Int. Cl.
*A61B 17/326* (2006.01)

(52) U.S. Cl.
CPC .................... *A61B 17/326* (2013.01)

(58) Field of Classification Search
CPC ................ A61B 17/326; A61B 17/11; A61B 2017/1132; A61B 17/08; A61B 17/32; A61B 17/32053
USPC ............. 606/39, 41, 108, 118, 120, 131, 139, 606/144, 148, 149, 150, 151, 153, 157, 158, 606/201, 203; 24/16 PB, 20 EE, 24, 285, 24/248
See application file for complete search history.

(56) References Cited

U.S. PATENT DOCUMENTS

| 1,417,142 | A | * | 5/1922 | Couch | 606/118 |
| 1,751,927 | A | * | 3/1930 | Kielberg | 292/256.6 |
| 2,076,468 | A | | 4/1937 | La Breck | |
| 2,272,072 | A | | 2/1942 | Ross | |
| 2,294,852 | A | | 9/1942 | Smith | |
| 2,296,594 | A | | 9/1942 | Blais et al. | |
| 2,353,647 | A | * | 7/1944 | Carmichael | 606/118 |
| 2,484,132 | A | | 10/1949 | Turner | |
| 2,544,037 | A | * | 3/1951 | Moseley | 606/118 |
| 2,561,176 | A | | 7/1951 | Buckingham | |
| 2,563,366 | A | * | 8/1951 | Henri | 285/387 |
| 2,689,141 | A | * | 9/1954 | Kiekhaefer | 285/409 |

(Continued)

FOREIGN PATENT DOCUMENTS

| DE | 19851792 | 4/2000 |
| GB | 2379879 | 9/2003 |

(Continued)

*Primary Examiner* — Katherine Rodjom
*Assistant Examiner* — Christian Knauss (57) ABSTRACT

A circumcision clamp system and related methods of use. The clamp system includes an inner ring that is placed under the foreskin proximate to the corona of the glans penis, and an outer ring that clamps the foreskin against the inner ring. In an embodiment suitable for necrotic circumcisions, the inner and outer rings include one or more break-off sections that enable a clinician to adjust the diameter of the clamp accordingly. The inner ring includes a key and lock arrangement that ensures the inner ring maintains a circular shape by denying all degrees of freedom to the joined sections thereof. The outer ring includes a plurality of clamping members extending radially inward from an inner surface thereof. In some embodiments, the outer ring includes castellations that work in cooperation with longitudinal grooves in the inner ring to aid in suture placement.

16 Claims, 4 Drawing Sheets

(56) References Cited

U.S. PATENT DOCUMENTS

| | | | |
|---|---|---|---|
| 2,695,616 A | 11/1954 | Hansell | |
| 3,048,177 A * | 8/1962 | Takaro | 606/153 |
| 3,056,407 A | 10/1962 | Kariher et al. | |
| 3,059,645 A * | 10/1962 | Hasbrouck et al. | 604/179 |
| 3,072,126 A | 1/1963 | Fenton | |
| 3,111,124 A * | 11/1963 | Rodbard | 606/118 |
| 3,254,650 A * | 6/1966 | Collito | 606/153 |
| 3,491,751 A * | 1/1970 | Wolfing | 601/41 |
| 3,612,057 A * | 10/1971 | Freedman | 606/118 |
| 3,789,848 A | 2/1974 | Honjyo | |
| 3,892,242 A | 7/1975 | Honjyo | |
| 3,913,187 A * | 10/1975 | Okuda | 24/484 |
| 4,365,144 A * | 12/1982 | Reich et al. | 219/535 |
| 4,491,136 A * | 1/1985 | LeVeen | 606/118 |
| 4,657,019 A * | 4/1987 | Walsh et al. | 606/153 |
| 4,708,512 A * | 11/1987 | Allert | 403/344 |
| 4,733,666 A * | 3/1988 | Mercer, Jr. | 606/151 |
| 4,881,760 A | 11/1989 | Runkles et al. | 285/93 |
| 5,163,943 A * | 11/1992 | Mohiuddin et al. | 606/118 |
| 5,269,788 A * | 12/1993 | Nelson, III | 606/118 |
| 5,439,466 A | 8/1995 | Kilejiam | |
| 5,609,626 A * | 3/1997 | Quijano et al. | 623/1.24 |
| 5,649,933 A | 7/1997 | Singh | |
| 5,797,921 A * | 8/1998 | Cimini et al. | 606/118 |
| 5,860,988 A | 1/1999 | Rawlings | |
| 5,913,521 A * | 6/1999 | Sangren et al. | 277/372 |
| 5,989,567 A * | 11/1999 | Dolisi | 424/400 |
| 6,254,613 B1 | 7/2001 | Harrison | |
| 6,523,866 B2 * | 2/2003 | Lin | 285/410 |
| 6,547,797 B1 * | 4/2003 | Lee | 606/118 |
| 6,579,227 B2 | 6/2003 | Haughey | |
| 6,660,012 B2 | 12/2003 | Lahiji | |
| 6,780,194 B2 | 8/2004 | Freedman et al. | |
| 7,303,567 B1 | 12/2007 | Smith | |
| 7,402,164 B2 * | 7/2008 | Watson et al. | 606/120 |
| 7,591,824 B2 | 9/2009 | Dave et al. | |
| 8,356,390 B2 * | 1/2013 | Flynn et al. | 24/270 |
| 2004/0215210 A1 | 10/2004 | Duel | |
| 2005/0258648 A1* | 11/2005 | Newman | 285/364 |
| 2006/0004392 A1* | 1/2006 | Amarant | 606/153 |
| 2007/0244516 A1* | 10/2007 | Chiu et al. | 606/207 |
| 2008/0004621 A1 | 1/2008 | Dahla et al. | |
| 2008/0004631 A1 | 1/2008 | Tomlinson | |
| 2008/0004654 A1 | 1/2008 | Tomlinson | |
| 2008/0021482 A1 | 1/2008 | Tomlinson | |
| 2008/0154283 A1* | 6/2008 | Shang | 606/118 |
| 2008/0174113 A1* | 7/2008 | Brimson | 285/368 |
| 2008/0195116 A1 | 8/2008 | Mansour | |
| 2009/0158559 A1* | 6/2009 | Chardon et al. | 24/16 PB |
| 2011/0098718 A1* | 4/2011 | Shang | 606/118 |
| 2011/0118766 A1* | 5/2011 | Reichenbach et al. | 606/153 |
| 2012/0203242 A1* | 8/2012 | Fuerst et al. | 606/118 |
| 2013/0296890 A1* | 11/2013 | Sgarzani et al. | 606/142 |

FOREIGN PATENT DOCUMENTS

| | | |
|---|---|---|
| SU | 1232234 | 5/1986 |
| SU | 1683702 | 10/1991 |
| WO | WO02/006329 | 8/2002 |
| WO | WO2005/039424 | 5/2005 |
| WO | WO2007/028378 | 3/2007 |

* cited by examiner

CLAMP FOR MALE CIRCUMCISION AND RELATED METHOD OF USE

CROSS REFERENCE TO RELATED APPLICATION

The present application claims the benefit of and priority to U.S. Provisional Application Ser. No. 61/490,679, filed on May 27, 2011, the entire contents of which are incorporated herein by reference.

BACKGROUND

1. Technical Field

The present disclosure generally relates to the field of circumcision, and more particularly, the present disclosure relates to apparatus and methods for reducing hemorrhaging, improving suture placement, and improving surgical outcomes during male circumcision procedures. Fixed size and adjustable size apparatus are presented with related methods of use.

2. Background of Related Art

The foreskin, or prepuce, is the retractable sheath of skin that covers the head, or glans, of a penis. The outside of the foreskin is a continuation of the skin on the shaft of the penis, while the inner foreskin includes mucous membrane, similar to the inside of the eyelid. Male circumcision is a procedure whereby the foreskin is removed, typically for health, religious, or cultural reasons.

Conventional circumcision may be performed by applying a local anesthetic to the penis, applying an appropriately-sized clamp to the foreskin, removing the foreskin using a scalpel or scissors, and suturing the wound. Alternatively, the foreskin may be clamped in a necrosing device such as a Shang Ring, whereby the foreskin is drawn over a first ring, a second ring is positioned on the foreskin outside the first ring, and the foreskin is crushed between the two rings, which in about a week results in necrosis of the foreskin. In each case, the penis must first be measured, or sized, to determine which diameter clamp to use during the procedure.

Conventional circumcision techniques may have drawbacks. In one respect, conventional devices require the practitioner to have considerable skill in order to avoid complications such as excessive hemorrhaging, infection, and/or permanent insult to the penis. In another respect, a variety of clamp sizes need to be inventoried to accommodate differently-sized penises. This may create logistical challenges, particularly in rural or remote regions where access to supply chains are limited. In another respect, necrotic techniques and clamps typically require a follow-up visit to a medical facility so that the device may be removed. The need for follow-up visits can be problematic in rural or remote areas, where lack of transportation, harsh terrain, or long distances may hinder or preclude a patient from returning to the doctor.

SUMMARY

The present disclosure is directed to a circumcision system for surgically removing excess foreskin from a penis. In some embodiments, a circumcision clamp system in accordance with the present disclosure includes a ring clamp having an open position and a closed position, The ring clamp includes a first semicircular portion having a first clasp end, and a first hinge end. The ring clamp further includes a second semicircular portion having a second clasp end, and a second hinge end pivotably joined to the first hinge end of the first semicircular portion. The ring clamp includes one or more castellations radially disposed about a periphery of the ring clamp and projecting longitudinally therefrom, defining one or more slots therebetween. The disclosed circumcision clamp system includes a generally cylindrical collar having a distal end and a proximal end and having one or more longitudinal grooves defined on an outer surface thereof. The ring clamp and a distal end of the generally cylindrical collar are adapted to clamp tissue (e.g., male foreskin) therebetween. The circumcision clamp system in accordance with claim 1, wherein the first clasp end includes an outer interlocking member having an outer pawl and the second clasp end includes an inner interlocking member having an inner pawl. A diameter of a proximal end of the collar may be greater than a diameter of a distal end of the collar. The outer surface of the distal end the collar may include a soft lining. The ratio of the number of longitudinal grooves of the collar to the number of castellations of the ring clamp may be about 5:1.

In another embodiment in accordance with the present disclosure, a circumcision clamp system includes an elongate inner support member having a first end and a second end. The first end and the second end are configured to operably engage to form an inner ring. A portion of the inner support member is selectively removable to change the diameter of the inner ring. In some embodiments, a portion of second end of the inner support member may be broken away to shorten the inner support member, which, in turn, decreases the diameter of the inner ring formed therefrom. The inner support member may include one or more scored portions to facilitate breaking off a section thereof. The disclosed circumcision clamp system includes an outer support member having a first end and a second end. The first end and the second end of the outer support member are configured to operably engage to form an outer ring. A portion of the outer support member is selectively removable to change the diameter of the outer ring. In some embodiments, a portion of second end of the outer support member may be broken away to shorten the outer support member, which, in turn, decreases the diameter of the outer ring formed therefrom. The outer support member may include one or more scored portions to facilitate breaking off a section thereof. The outer ring includes a plurality of clamping elements extending radially inward from an inner surface thereof. The inner ring and plurality of clamping elements are adapted to clamp tissue, e.g., male foreskin, therebetween. The outer support member may include a plurality of clamping segments. The clamping segments may be joined by a living hinge. A clamping segment may include a clamping element.

A disclosed circumcision clamp system may include a clasp assembly configured to join the first end and the second end of the outer support member. The clasp assembly may include an outer interlocking member having an outer pawl, and an inner interlocking member having an inner pawl. The outer interlocking member may be associated with a first end of an inner support member or an outer support member. The inner interlocking member may be associated with a second end of an inner support member or an outer support member.

A circumcision clamp system in accordance with the present disclosure may include an inner support that further includes a generally semicircular key having a coupling end and a base and extending from the first end of the inner support. One or more undercuts may be defined at the base of the key. The undercuts are configured to operably engage a corresponding lock included in a second end of the inner support. The inner support may include one or more walls extending from an outer surface of the inner support partially enclosing the one or more undercuts.

A circumcision clamp system in accordance with the present disclosure may include an inner support that further includes a generally semicircular lock defined in a second end thereof that includes one or more lobes configured to operably engage a corresponding undercut defined in the first end of the inner support.

Also disclosed herein is a method of performing male circumcision. In some embodiments, the disclosed method includes the steps of determining penis size within a set of standard penis sizes. A circumcision clamp is selected in accordance with the determined penis size. A generally cylindrical collar having a distal end and a proximal end and having one or more longitudinal grooves defined in an outer surface thereof is positioned around the corona of the glans penis. A small coaxial incision is made in the foreskin around the corona of the glans penis. The foreskin is rolled proximally toward a distal end of the cylindrical collar. A ring clamp in an open position is positioned around the foreskin. The ring clamp is closed around the foreskin to clamp the foreskin between the cylindrical collar and the ring clamp. The excess foreskin is removed, e.g., using scalpel or scissors. The open foreskin tissue is sutured, and the ring clamp and the cylindrical collar are removed from the penis. The provided ring clamp may include a first semicircular portion having a first clasp end and a first hinge end, and a second portion having a second clasp end and a second hinge end pivotably joined to the first hinge end of the first semicircular portion. The provided ring clamp may include one or more castellations radially disposed about a periphery of the ring clamp and projecting proximally therefrom and defining one or more slots therebetween. The disclosed method may additionally include passing a suturing needle through a slot, passing the suturing needle through open foreskin tissue, and guiding the suturing needle in cooperation with a longitudinal groove defined in an outer surface of the cylindrical collar.

BRIEF DESCRIPTION OF THE DRAWINGS

Various embodiments of the present disclosure are described hereinbelow with references to the drawings, wherein.

DETAILED DESCRIPTION

Particular embodiments of the present disclosure are described hereinbelow with reference to the accompanying drawings; however, the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions.

In the drawings and in the descriptions that follow, terms referencing orientation, e.g., "top", "bottom", "up", "down", "left", "right", and the like, are used for illustrative purposes with reference to the figures and features shown therein. Embodiments in accordance with the present disclosure may be practiced in any orientation without limitation.

Figure 1:
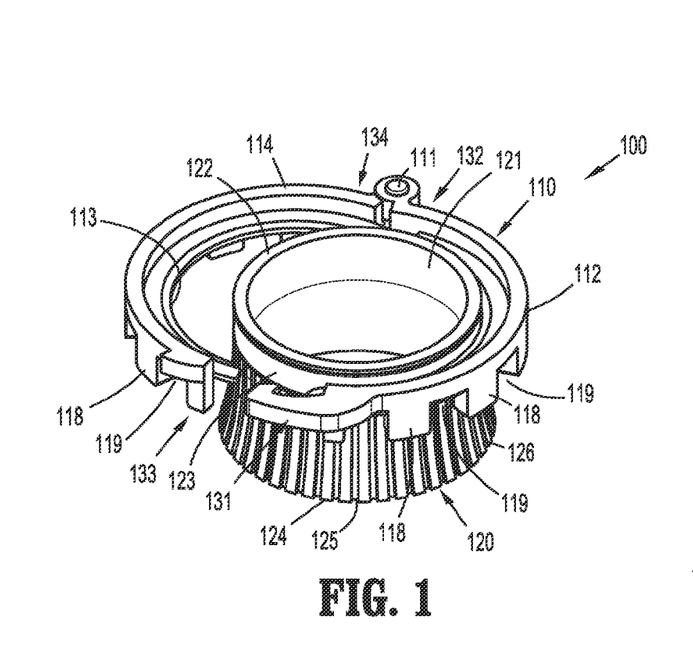
FIG. 1 is a perspective view of an embodiment of a circumcision clamp system in accordance with the present disclosure showing a clamp in an open position.
Figure 2:
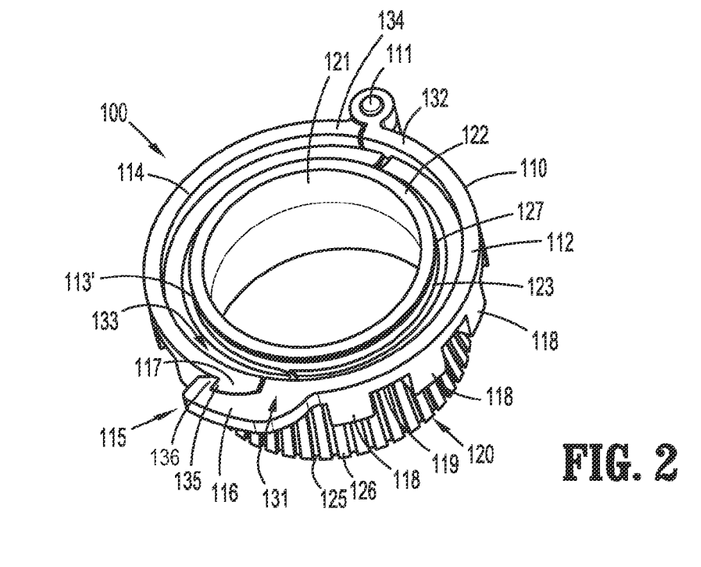
FIG. 2 is a perspective view of the circumcision clamp system shown in FIG. 1 showing the clamp in a closed position.

Referring to FIG. 1, a circumcision clamp system 100 is presented. The circumcision clamp system 100 includes a hinged clamp 110 and a generally cylindrical collar 120. Hinged clamp 110 includes a first semicircular portion 112 having a clasp end 131 and a hinged end 132, and a second semicircular portion 114 having a clasp end 133 and a hinged end 134. First semicircular portion 112 and second semicircular portion 114 are joined at the respective hinged ends 132, 134 thereof by a hinge 111 that enables the semicircular portions 112, 114 of clamp 110 to move between an open position as exemplified in FIG. 1, and a closed position as shown in FIG. 2.

The respective clasp ends 131 and 133 of first semicircular portion 112 and second semicircular portion 114, respectively, include a cooperatively interlocking clasp 115 (FIG. 2) that is configured to retain first semicircular portion 112 and second semicircular portion 114 in the closed position during use. At a clasp end 131 thereof, semicircular portion 112 includes an outer interlocking member 116 having an outer pawl 136 (FIG. 2). Outer pawl 136 is configured to operably engage a mating inner pawl 135 of inner interlocking member 117 that is disposed at a clasp end 133 of semicircular portion 114. In some embodiments, semicircular portion 112 and semicircular portion 114 are formed from material that enables outer interlocking member 116 and inner interlocking member 117 to radially deflect when first semicircular portion 112 and second semicircular portion 114 are moved between a closed position and an open position, e.g., enabling outer interlocking member 116 to ride over inner interlocking member 117 to facilitate the cooperative engagement and/or disengagement thereof. An inner clamping portion 113 projects radially inward from first semicircular portion 112 and second semicircular portion 114. When first semicircular portion 112 and second semicircular portion 114 are in the closed position, inner clamping portion 113 cooperates with one end 122 of collar 120 to grasp foreskin tissue therebetween during a circumcision procedure. Advantageously, the diameter of clamping portion 113 is slightly larger than end 122 of collar 120, such that during a circumcision procedure, tissue may be clamped sufficiently between inner clamping portion 113 and collar 120 to minimize bleeding and to promote hemostasis, without crushing the tissue. In some embodiments, the clearance between clamping portion 113 and end 122 of collar 120 is in a range of about 0.025" to 0.050".

Figure 3:
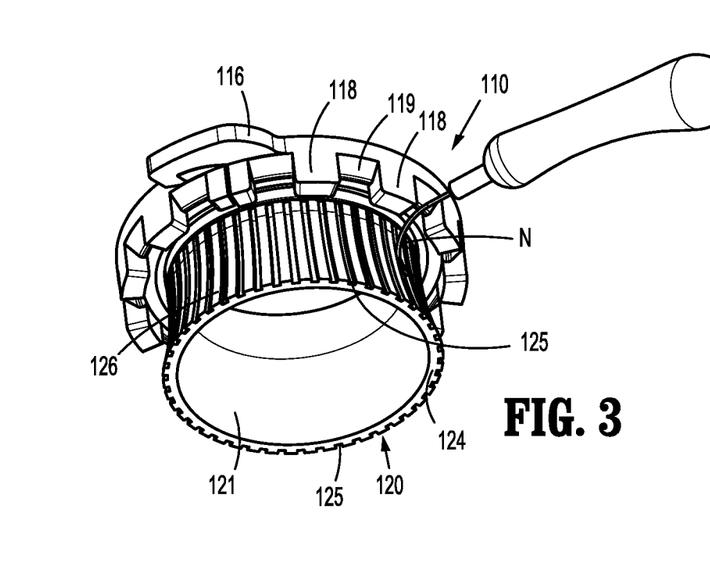
FIG. 3 is a perspective view of the circumcision clamp system shown in FIG. 1 showing a relationship between a ring and a suturing needle.
Figure 4:
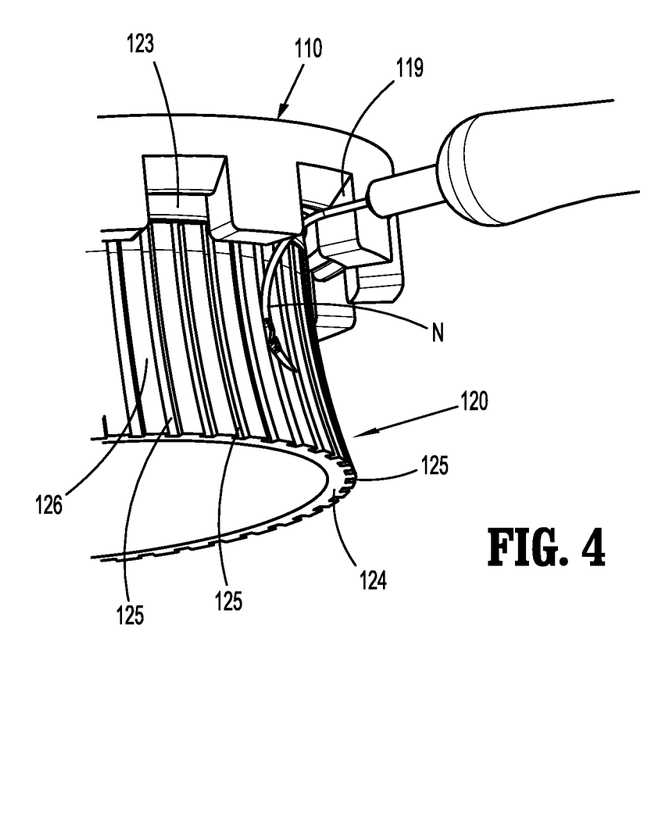
FIG. 4 is a detail perspective view of the circumcision clamp system shown in FIG. 1 showing a relationship between a ring and a suturing needle.

As best seen in FIGS. 3 and 4, clamp 110 includes a plurality of radially-arranged castellations 118 projecting laterally and proximally from a proximal edge of clamp 110. A plurality of slots 119 are defined between the castellations 118. During use, one or more of the slots 119 may be used as a suture guide, which may assist a surgeon to evenly suture a wound, using a sufficient number of sutures.

Circumcision clamp system 100 includes an annular collar 120 having an end 122 having a first diameter and an end 124 having a second diameter that is greater than the first diameter of end 122. In some embodiments, the diameter of collar 120 increases from the first diameter to the second diameter in a flared (e.g., exponential) manner, as depicted in FIGS. 1-4. In some embodiments, the diameter of collar 120 may increase from the first diameter to the second diameter in a linear (e.g., straight) manner. An outer surface 126 of collar 120 includes a plurality of longitudinal grooves 125 defined therein. Each longitudinal groove 125 is configured to accommodate the width of a suturing needle used during circumcision procedures. For example, and without limitation, longitudinal groove 125 is dimensioned to accommodate a Surgipro CV-24½ circle, 20 mm needle. During use, a longitudinal groove may further assist a surgeon to neatly and evenly suture an incision by enabling the suturing needle to capture both layers of the skin, and/or keeping the suturing needle oriented longitudinally as the sutures are stitched into tissue.

Collar 120 may include a lining 123 formed about end 122 thereof. Lining 123 may be formed from an elastomeric or resilient material, such as, silicone, rubber, or the like. Alternatively, the use of other known resilient materials is envisioned. In some embodiments, lining 123 may be joined to collar 120 by overmolding.

During use of circumcision clamp 100, a surgeon may administer antiseptic and local anesthesia to the penis. The penis is then sized to determine clamp system size. It is envisioned that circumcision clamp system 100 be provided in one or more sizes, e.g., diameters, to accommodate use with penises of differing girths. The desired clamp size is selected, and end 122 of collar 120 is positioned around the corolla of the glans penis. Next, a small coaxial incision is made in the foreskin. The foreskin is then rolled over itself, generally proximally and over end 122 of collar 120. Hand instruments may be used to manipulate the foreskin into position over collar 120. Hinged clamp 110 in its open position is then positioned around the foreskin and end 122 of collar 120, and the clamp 110 is closed, e.g., clasp 115 is engaged, thereby clamping the foreskin between clamping portion 113 and distal end 122 of collar 120. The excess foreskin is then removed using any suitable manner of resection, including without limitation using scissors or a scalpel. The wound is then stitched by passing a suturing needle through a slot 119 and through the open foreskin tissue. Advantageously, the collar 120 protects the corona and glans penis from accidental puncture by the needle, while slots 119 assist in placing the stitches uniformly about the penis. Lateral grooves 125 in collar 120 help to guide the needle under the edge of the skin, to capture both edges of the foreskin during suturing, and may further assist the surgeon in placing the stitches uniformly. After closing the wound (e.g., all stitches have been placed), the clasp 115 of hinged clamp 110 is released, and clamp 110 and collar 120 are removed from the penis. The wound is then dressed in accordance with standard medical practice.

Figure 5:
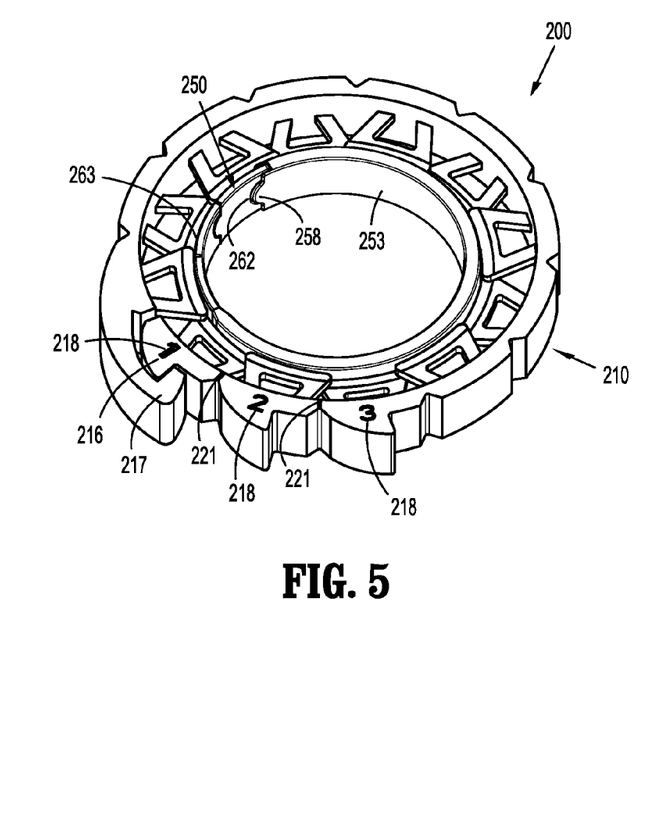
FIG. 5 is a perspective view of an alternative embodiment of the presently disclosed circumcision clamp system including an adjustable circumcision ring and an adjustable circumcision clamp in accordance with the present disclosure.
Figure 6:
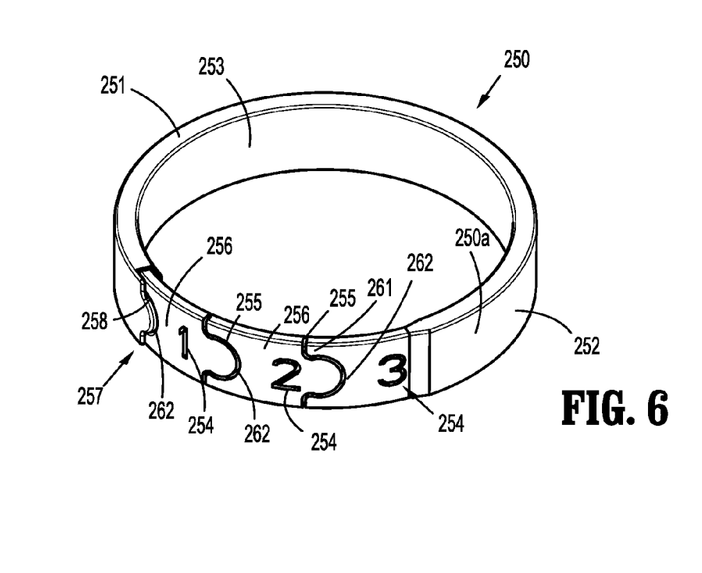
FIG. 6 is a perspective view of the adjustable circumcision ring shown in FIG. 5.

Referring now to FIGS. 5-8, another embodiment of a circumcision clamp system 200 in accordance with the present disclosure is shown. The disclosed universal adjustable clamp system 200 may be used for necrotic circumcision procedures and includes an adjustable outer ring 210 (FIG. 7) and an adjustable inner ring 250 (FIG. 6). Inner ring 250 and outer ring 210 include one or more removable segments 256, 218, respectively, that may be broken off to enable clamp system 200 to be configured for use with penises of different size.

Inner ring 250 includes body portion 250a and one ore more removable segments 256. Ring 250 defines an inner surface 253 which, during use, is positioned generally towards the glans penis and an outer surface 252 which is positioned generally toward the inner foreskin membrane. Body portion 250a includes a key end 257 and a lock end 262 which may be selectively coupled to form the ring, or uncoupled to enable sizing as described below. Each removable segment 256 also includes a lock end 262 which may be selectively coupled to key end 257 to form ring 250.

Figure 6A:
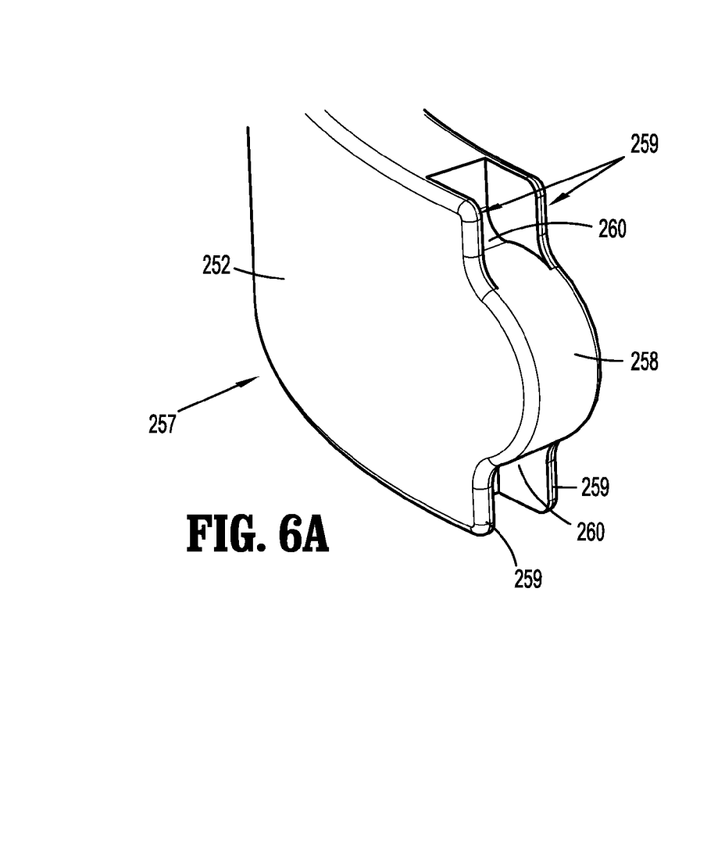
FIG. 6A is a detail perspective view of a portion of the adjustable circumcision ring shown in FIG. 5.

With particular reference to FIG. 6A, key end 257 includes a key 258 extending therefrom having a generally semicircular shape. One or more undercuts 260 are defined in the base of key 258 that correspond in shape to lock ends 262 of body portion 250a and removable segments 256. Each lock end 262 has a generally semicircular shape corresponding to key 258 and includes one or more lobes 261 that are configured to mate with corresponding undercuts 260 of key end 257, enabling key 258 to fixedly "snap" into lock end 262 to couple the mating ends to form inner ring 250. A portion of the outer surface 252 of inner ring 250 extends beyond undercuts 260 to form two pairs of walls 259, one on each side of key 258. When a lock end 262 is secured to key 258, walls 259 confine lobes 261 within undercuts 261 thereby imparting rigidity to the structure of inner ring 250. In some embodiments, walls 259 and undercuts 260 cooperate to deny some or all degrees of freedom to the joined ends of inner ring 250. Inner ring 250 may be formed from any suitable biocompatible material that promotes even curvature and is capable of assuming a circular shape when inner ring 250 is in a coupled configuration. In some embodiments, inner ring 250 may be formed from polymeric material, including without limitation, polypropylene, polyethylene, polyvinyl chloride, nylon, ABS, and/or Radel® polyphenylsulfone (PPSU) manufactured by Solvay Plastics of Brussels, Belgium.

Removable segments 256 may be selectively removed, or "snapped off" body portion 250a along one or more scored break lines 255 to facilitate sizing of inner ring 250. For example, one removable segment may be removed from body portion 250a to decrease the diameter of inner ring 250 to a first extent, or two removable segments 256 may be removed from body portion 250a to reduce the diameter of inner ring 250 to a second extent. Inner ring 250 may include one or more identification numbers 254 that correspond to standard penis sizes. During use, a clinician may size a patient's penis using a standardized gauge. If necessary, the clinician may then uncouple the inner ring 250, break off the unwanted removable segments 256, and re-couple the inner ring 250. The one or more break lines 255 are configured to enable facile separation of the removable segments 256 and to leave a clean, newly-exposed lock end 262 that, in turn, may be coupled to key 258 as previously described. Although two removable segments 256 are shown in the figures, inner ring 250 may include one or more removable segments 256, e.g., four.

Figure 7:
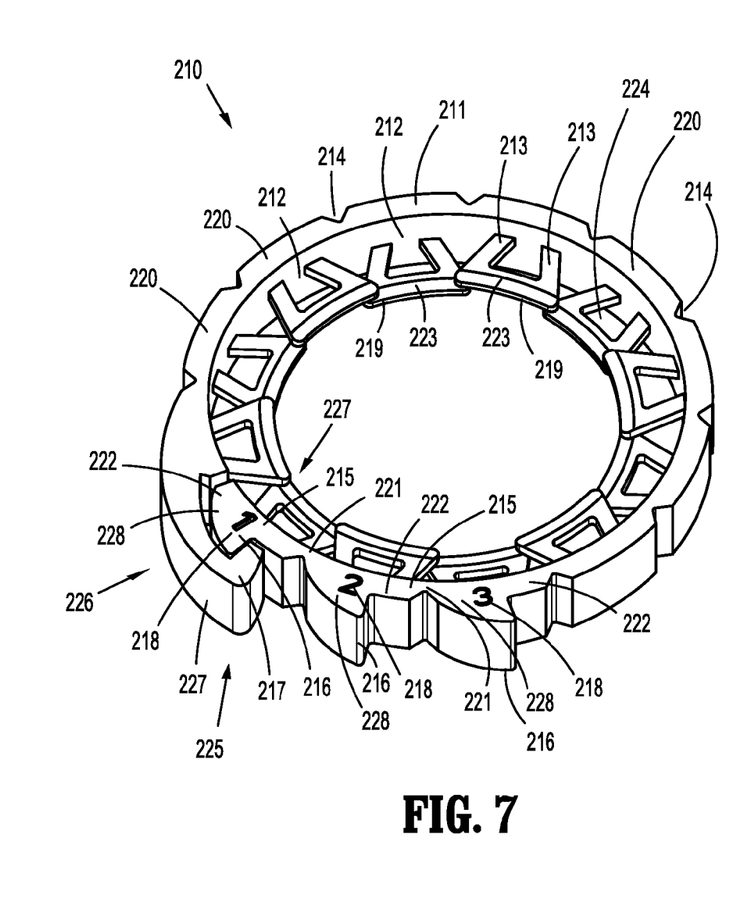
FIG. 7 is a perspective view of the adjustable circumcision clamp shown in FIG. 5.

Adjustable outer ring 210 includes a plurality of clamping segments 220 having a first end 226 and a second end 227. Outer ring 210 may be arranged in a generally circular configuration, e.g., a closed position, wherein a clasp assembly 225 joins first end 226 and a second end 227 of outer ring 210. Alternatively, outer ring 210 may be configured in an open position wherein first end 226 and a second end 227 are not joined. Clasp 225 includes an outer interlocking member 227 having an outer pawl 217 and an inner interlocking member 228 having an inner pawl 216. Outer pawl 217 and inner pawl 216 are designed to selectively and releasably engage one another to join first end 226 and second end 227 of outer ring 210. Each of the plurality of clamping segments 220 are joined to at least one adjacent clamping segment 220 by a living hinge 214 that enables outer ring 210 to flex between an open position and a closed position.

Adjustable outer ring 210 includes one or more removable segments 222 that may be selectively removed, or "snapped off", along one or more scored break lines 221 to facilitate the sizing of outer ring 250. Each of the one or more removable segments 222 includes an inner interlocking member 228 an inner pawl 216 associated therewith to facilitate clamping when another removable segment 222 has been removed. The one or more removable segments 222 include one or more identification numbers 218 that correspond to standard penis sizes. During use, similarly-numbered sections of inner ring 250 and outer ring 210 may be broken off to enable mutually cooperative sizing of inner ring 250 and outer ring 210 for use. Advantageously, this disclosed arrangement provides a controlled gap 263 between an outer surface 252 of inner ring 250 and the one or more clamping faces 219 of outer ring 210, as described in detail below. The controlled gap 263 is configured to clamp foreskin tissue with sufficient force to ensure hemostasis with sufficient pressure to promote necrosis but without excessive pressure that will cause the tissue to break. In this manner, improved circumcision outcomes may be attained while minimizing complications or undue discomfort.

A clamping element 223 extends radially inward from an inner surface 212 of one or more clamping segments 220 and/or removable segments 222. In the illustrated embodiment, clamping element 223 has a generally open trapezoidal shape and includes a clamping face 219 that is joined to an inner surface 212 of clamping segment 220 by a pair of posts 213 defining generally trapezoidal opening 224. Alternatively, clamping elements 223 may be secured or formed on an inner surface of clamping segments 223 in a variety of different manners using a variety of different techniques. Posts 213 may be resilient, e.g., may flex slightly to promote even distribution of a clamping force. In some embodiments, clamping element 223 may have a closed trapezoidal shape (e.g., having no opening 224), or any other suitable shape. The one or more clamping elements 223 are arranged in a staggered configuration to facilitate overlapping of the adjacent surfaces of neighboring clamping elements 223 when the clamp 200 is in use. This overlapping arrangement ensures an effectively continuous clamping surface is provided by the plurality of clamping faces 219 when the outer ring 210 is positioned around the foreskin.

Outer ring 210 may be formed from any suitable biocompatible material that promotes operation of living hinges 214 and is capable of generating sufficient clamping force for clamping element 223. In some embodiments, outer ring 210 may be formed from polymeric material, including without limitation, polypropylene, and polyethylene.

During use, a surgeon may administer antiseptic and local anesthesia to the penis. The penis is then sized to determine which, if any, inner ring 250 removable segments 256 and outer ring 210 removable segments 222 need to be removed.

If sizing indicates that one or more segments need to be removed, inner ring 250 and outer ring 210 are re-sized by removing one or more segments 256 and 222 from the inner and outer rings 250 and 210, respectively. To remove a segment 256 from inner ring 250, key end 257 and lock end 262 of inner ring 250 are uncoupled, the desired removable segments 256 are broken off, and the key end 257 and newly-exposed lock end 262 are coupled to re-form inner ring 250.

To remove a segment 222 from outer ring 210, clasp assembly 225 of outer ring 210 is opened, freeing first end 226 and second end 227, and one or more removable segments 222 of outer ring 210 are broken off as required.

Inner ring 250 is positioned around the glans penis underneath the foreskin. The foreskin may optionally be retracted distally to expose the glans penis, facilitating placement of inner ring 250 therearound, and the foreskin may be slid proximally, over inner ring 250.

The outer ring 210, in an open configuration, is positioned around the foreskin concentric to inner ring 250. The first end 226 and second end 227 of outer ring 210 are brought together and clasp 225 is engaged, thereby causing the one ore more clamping faces 219 to clamp foreskin tissue against outer surface 252 of inner ring 250 and, in turn, to cause hemostasis of the foreskin proximal of the clamp (e.g., cut off the foreskin blood supply) and, ultimately, necrosis of the foreskin proximal of the clamp. Antiseptic and/or dressing may be applied to the clamped tissue and/or surrounding tissue. The clamping system 200 is left in place on the penis for a predetermined period of time. In some embodiments, clamping system 200 is left in place for about a week. Prior to the expiration of the predetermined time period, the necrotic foreskin may become detached without further intervention. After the period of time has elapsed, the necrotic foreskin (if still attached) is removed. Clasp 225 of outer ring 210 is disengaged, allowing outer ring 210 to be opened and removed form the operative site. Inner ring 250 is removed form the penis. In some embodiments, clamping system 200 may be disposable, therefore inner ring 250 and outer ring 210 may be discarded.

It is to be understood that various modifications may be made to the embodiments disclosed herein. Further variations of the above-disclosed and other features and functions, or alternatives thereof, may be desirably combined into many other different systems, devices, and applications without departing from the spirit and scope of the present disclosure. Various presently unforeseen or unanticipated alternatives, modifications, variations or improvements therein may be subsequently made by those skilled in the art, which are also intended to be encompassed by the following claims.

What is claimed is:

1. A circumcision clamp system, comprising:
   a ring clamp having an open position and a closed position, the ring clamp comprising:
      a first semicircular portion having a first clasp end, and a first hinge end;
      a second semicircular portion having a second clasp end, and a second hinge end pivotably joined to the first hinge end, the ring clamp defining an inner clamping portion;
      a plurality of castellations radially disposed about a periphery of the ring clamp and projecting longitudinally therefrom, the plurality of castellations defining a plurality of slots that are configured to aid in suture placement; and
   a collar having a distal end and a proximal end;
   wherein the ring clamp is positioned about a distal end of the collar and is adapted to clamp tissue between the inner clamping portion of the ring clamp and the collar.

2. The circumcision clamp system in accordance with claim 1, wherein the ring clamp and the distal end of the collar are adapted to clamp male foreskin.

3. The circumcision clamp system in accordance with claim 1, wherein the first clasp end includes an outer interlocking member having an outer pawl and the second clasp end includes an inner interlocking member having an inner pawl.

4. The circumcision clamp system in accordance with claim 1, wherein a diameter of the proximal end of the collar is greater than a diameter of the distal end of the collar.

5. The circumcision clamp system in accordance with claim 1, wherein an outer surface of the distal end of the collar further includes a soft lining.

6. The circumcision clamp system in accordance with claim 1, wherein the collar includes one or more longitudinal grooves defined in an outer surface thereof.

7. The circumcision clamp system in accordance with claim 6, wherein a ratio of the number of longitudinal grooves to the number of castellations is about 5:1.

8. The circumcision clamp system in accordance with claim 1, wherein the collar is of unitary construction.

9. A circumcision clamp system, comprising:
- a ring clamp having an open position and a closed position, the ring clamp comprising:
- a first semicircular portion having a first clasp end, and a first hinge end;
- a second semicircular portion having a second clasp end, and a second hinge end pivotally joined to the first hinge end;
- a collar having a distal end and a proximal end and defining a longitudinal axis extending between the proximal and distal ends, the collar including a plurality of longitudinal grooves spaced from each other and extending along an outer surface thereof in a direction parallel to the longitudinal axis, each of the longitudinal grooves being dimensioned to accommodate a suture needle to aid in suture placement;
- wherein the ring clamp and a distal end of the collar are adapted to clamp tissue therebetween.

10. The circumcision clamp system in accordance with claim 9, further including a plurality of castellations radially disposed about a periphery of the ring clamp and projecting longitudinally therefrom, the plurality of castellations defining a plurality of slots that are configured to aid in suture placement.

11. The circumcision clamp system in accordance with claim 10, wherein a ratio of the number of longitudinal grooves to the number of castellations is about 5:1.

12. The circumcision clamp system in accordance with claim 9, wherein the first clasp end includes an outer interlocking member having an outer pawl and the second clasp end includes an inner interlocking member having an inner pawl.

13. The circumcision clamp system in accordance with claim 9, wherein a diameter of the proximal end of the collar is greater than a diameter of the distal end of the collar.

14. The circumcision clamp system in accordance with claim 9, wherein an outer surface of the distal end of the collar further includes a soft lining.

15. The circumcision clamp system in accordance with claim 9, wherein the collar is of unitary construction.

16. The circumcision clamp system in accordance with claim 9, wherein the longitudinal grooves extend from the proximal end of the collar to the distal end of the collar.

\* \* \* \* \*